United States Patent
Igarashi

(10) Patent No.: US 11,433,151 B2
(45) Date of Patent: *Sep. 6, 2022

(54) MICROBE INACTIVATION PROCESSING METHOD AND CELL ACTIVATION PROCESSING METHOD

(71) Applicant: Ushio Denki Kabushiki Kaisha, Tokyo (JP)

(72) Inventor: Tatsushi Igarashi, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/075,138

(22) Filed: Oct. 20, 2020

(65) Prior Publication Data
US 2021/0030906 A1    Feb. 4, 2021

Related U.S. Application Data

(62) Division of application No. 16/232,571, filed on Dec. 26, 2018, now Pat. No. 10,864,287.

(30) Foreign Application Priority Data

Dec. 27, 2017    (JP) ................................ 2017-251511

(51) Int. Cl.
    *A61L 2/10*          (2006.01)
    *G02B 5/20*         (2006.01)

(52) U.S. Cl.
    CPC ................ *A61L 2/10* (2013.01); *G02B 5/208* (2013.01); *A61L 2202/14* (2013.01)

(58) Field of Classification Search
    CPC ..... A61N 5/0616; A61L 2/10; A61L 2202/14; G02B 5/208
See application file for complete search history.

(56) References Cited

U.S. PATENT DOCUMENTS 6,787,782 B1   9/2004   Krosney et al.
7,306,620 B2   12/2007   Cumbie
(Continued)

FOREIGN PATENT DOCUMENTS

JP    2014-016618 A    1/2014
JP    2014-508612 A    4/2014
(Continued)

OTHER PUBLICATIONS

An Office Action; "Notice of Reasons for Refusal", mailed by the Japanese Patent Office dated Jun. 29, 2021 was, which corresponds to Japanese Patent Application No. 2017-251511 and is related to U.S. Appl. No. 17/075,138; with English language translation.
(Continued)

*Primary Examiner* — Wyatt A Stoffa
(74) *Attorney, Agent, or Firm* — Studebaker & Brackett PC

(57) ABSTRACT

Disclosed are a microbe inactivation processing method that can perform inactivation processing of microbes, while damage to human body cells is prevented or inhibited, with an efficient use of light emitted from a light source and the obtainment of a large effective irradiation area. Also provided are a cell activation processing method that can reliably activate target cells with high efficiency. The microbe inactivation processing method includes: a step of applying light emitted from a light source through an optical filter, with the light source configured to emit light having a wavelength within a wavelength range of 190 nm to 237 nm, in order to perform inactivation processing of a target microbe. When the light emitted from the light source is incident at an incident angle of 0°, the optical filter transmits at least a part of ultraviolet light having a wavelength within a range of not lower than 190 nm and not more than 230 nm, and transmits at least a part of ultraviolet light having a
(Continued)

wavelength within a range of more than 230 nm and not more than 237 nm, and the optical filter blocks transmission of ultraviolet light having a wavelength out of a wavelength range of not lower than 190 nm and not more than 237 nm.

7 Claims, 4 Drawing Sheets

(56) References Cited

U.S. PATENT DOCUMENTS

| | | | |
|---|---|---|---|
| 7,738,192 | B1 | 6/2010 | Tobey et al. |
| 10,071,262 | B2* | 9/2018 | Randers-Pehrson ... A61B 18/18 |
| 2003/0018373 | A1 | 1/2003 | Eckhardt et al. |
| 2007/0255266 | A1* | 11/2007 | Cumbie .............. A61N 5/0624 606/9 |
| 2008/0199354 | A1 | 8/2008 | Gordon |
| 2010/0028201 | A1 | 2/2010 | Neister |
| 2010/0222852 | A1 | 9/2010 | Vasily et al. |
| 2010/0226029 | A1 | 9/2010 | Funasaka |
| 2013/0048876 | A1 | 2/2013 | Crawford |
| 2014/0039582 | A1 | 2/2014 | Wilson et al. |
| 2017/0173195 | A1* | 6/2017 | Stibich .................. A61L 2/10 |
| 2017/0304472 | A1 | 10/2017 | Neister et al. |
| 2017/0357033 | A1 | 12/2017 | Ockenfuss et al. |
| 2018/0169279 | A1* | 6/2018 | Randers-Pehrson ........ A61L 2/0047 |
| 2019/0038914 | A1* | 2/2019 | Igarashi ................. G02B 5/28 |
| 2019/0227207 | A1 | 7/2019 | Nagaya et al. |
| 2020/0030469 | A1* | 1/2020 | Neister .................. B08B 17/00 |
| 2021/0187319 | A1* | 6/2021 | Randers-Pehrson ........ A61N 5/0601 |

FOREIGN PATENT DOCUMENTS

| | | |
|---|---|---|
| WO | 2017/135190 A1 | 8/2017 |
| WO | 2017/213047 A1 | 12/2017 |

OTHER PUBLICATIONS

Gupta A, Avci P, Dai T, Huang YY, Hamblin MR. Ultraviolet Radiation in Wound Care: Sterilization and Stimulation. Advances in Wound Care. Oct. 2013; 2(8):422-437. DOI: 10.1089/wound.2012.0366. (Year: 2013).

An Office Action; "Notice of Reasons for Refusal", mailed by the Japanese Patent Office dated Oct. 19, 2021, which corresponds to Japanese Patent Application No. 2021-152053 and is related to U.S. Appl. No. 17/075,138; with English language translation.

An Office Action; "Notice of Reasons for Refusal", mailed by the Japanese Patent Office dated Mar. 1, 2022, which corresponds to Japanese Patent Application No. 2021-152053 and is related to U.S. Appl. No. 17/075,138; with English language translation.

* cited by examiner

MICROBE INACTIVATION PROCESSING METHOD AND CELL ACTIVATION PROCESSING METHOD

CROSS-REFERENCE TO RELATED APPLICATIONS

This application is a Divisional of U.S. patent application Ser. No. 16/232,571 filed Dec. 26, 2018, which claims benefit of priority to Japanese Patent Application No. 2017-251511 filed Dec. 27, 2017, the entire content of which is incorporated herein by reference.

TECHNICAL FIELD

The present invention relates to a microbe inactivation processing method and a cell activation processing method using light irradiation.

BACKGROUND ART

So-called ultraviolet sterilization is performed by the action of ultraviolet light on DNA inside cells of target organisms such as germs. More specifically, the ultraviolet light absorbed by the DNA inside the cells destroys a genetic code of the DNA, and so the target organisms are inactivated so as to prevent the normal growth and metabolism of the cells.

However, since the genetic code of the DNA in the cells of the organisms is destroyed in the ultraviolet sterilization, as described above, applying the ultraviolet light to human bodies damages normal cells of the human bodies, as a matter of course. As a result, for example, serious problems including photoaging, skin cancer and the like occur in the human bodies.

For example, it is known that the application of UV-C having a wavelength of 200 to 280 nm may cause development of cancer in humans owing to damage to DNA. It is also known that the application of UV-B having a wavelength of 280 to 315 nm may cause development of cancer, and there is a strong likelihood of the occurrence of melanoma, which is particularly dangerous. On the other hand, it is known that, when UV-A having a wavelength of 315 to 380 nm is applied, there is a weak likelihood of the occurrence of cancer.

Therefore, the ultraviolet sterilization has not conventionally become widespread as a method for sterilizing harmful microbes present in the human bodies.

In consideration of the circumstances as described above, a sterilization device that selectively inactivates target organisms, i.e., bacteria, without damaging human cells has been proposed in recent years (refer to Patent Literature 1). In the sterilization device, considering that the bacteria are typically and physically much smaller than the human cells in size, the wavelength of ultraviolet light to be applied is appropriately selected. To be more specific, ultraviolet light having a wavelength of 190 to 230 nm is applied to a sterilization target portion of a human body with the use of a light source, such as a KrBr excimer lamp that emits light having a center wavelength of 207 nm or a KrCl excimer lamp that emits light having a center wavelength of 222 nm, and an optical filter for blocking transmission of ultraviolet light having a wavelength of lower than 190 nm and more than 230 nm. Therefore, target organisms that are present in the sterilization target portion of the human body are inactivated, while the risk of damage to the human cells is substantially prevented.

CITATION LIST

Patent Literature

Patent Literature 1: Japanese Translation of PCT Patent Application Publication No. 2014-508612

SUMMARY OF INVENTION

Technical Problem

However, it is found out that such a sterilization device practically has the following problems.

In the above-described sterilization device, an interference filter having a dielectric multilayer film made of $SiO_2/Al_2O_3$ or $SiO_2/MgF_2$ is used as an optical filter in order to transmit light having a wavelength within a wavelength range of 190 to 230 nm of light emitted from the light source, and cut light out of the wavelength range.

The interference filter has a spectral transmission characteristic having a sharp curve between cut-off and cut-on wavelengths. On the other hand, the interference filter has incident angle dependence in which light transmittance depends on an incident angle.

More specifically, the interference filter has an optical characteristic that the peak wavelength of the light transmittance and a wavelength on a long-wavelength side end of a transmittance range shift to a short-wavelength side with an increase in the incident angle of light.

Accordingly, when light emitted from the light source is applied through the interference filter, the interference filter blocks or significantly attenuates light that is incident on the interference filter at a large incident angle, of the light emitted from the light source, thus making it difficult to use the light emitted from the light source with high efficiency.

Since the interference filter blocks or attenuates light having been incident at a large incident angle, light outputted through the interference filter has a small diffusion angle, thus making it difficult to obtain a large effective irradiation area in the sterilization target portion.

The present invention has been made in view of the foregoing circumstances and has as its object the provision of a microbe inactivation processing method that can subject target microbes that are present on or in a human body (particularly, in an injury or an operative field) to inactivation processing, while damage to human body cells is prevented or inhibited, with an efficient use of light emitted from a light source, and the obtainment of a large effective irradiation area.

The present invention has as another object the provision of a cell activation processing method that can reliably activate target cells with high efficiency.

Solving Means

To solve the foregoing problems, as a result of diligent study of the present inventors, they have found that the application of ultraviolet light having a wavelength of more than 230 nm and not more than 237 nm does not damage human body cells. The inventors have thus completed the present invention on the basis of the findings.

A microbe inactivation processing method according to the present invention includes a step of applying light emitted from a light source through an optical filter, with the light source configured to emit light having a wavelength within a wavelength range of 190 nm to 237 nm, in order to perform inactivation processing of a target microbe, wherein when the light emitted from the light source is incident at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength out of a wavelength range of not lower than 190 nm and not more than 237 nm.

A microbe inactivation processing method according to the present invention includes a step of applying light emitted from a light source through an optical filter, with the light source configured to emit the light having a wavelength within a wavelength range of 190 nm to 237 nm, in order to perform inactivation processing of a target microbe, wherein when the light emitted from the light source is incident at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength within wavelength ranges of UV-B and UV-C excluding a wavelength range of not lower than 190 nm and not more than 237 nm.

A cell activation processing method according to the present invention includes a step of applying light emitted from a first light source through an optical filter, and applying light emitted from a second light source, with the first light source configured to emit the light having a wavelength within a wavelength range of 190 nm to 237 nm and the second light source configured to emit the light having a wavelength in an infrared range, in order to perform activation processing of cells in a light irradiation area, wherein when the light emitted from the first light source is incident at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength out of a wavelength range of not lower than 190 nm and not more than 237 nm.

A cell activation processing method according to the present invention includes a step of applying light emitted from a first light source through an optical filter, and applying light emitted from a second light source, with the first light source configured to emit light having a wavelength within a wavelength range of 190 nm to 237 nm and the second light source configured to emit light having a wavelength in an infrared range, in order to perform activation processing of cells in a light irradiation area, wherein when the light emitted from the first light source is incident at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength within wavelength ranges of UV-B and UV-C excluding a wavelength range of not lower than 190 nm and not more than 237 nm.

In the cell activation processing method according to the present invention, it is preferable that, after a predetermined time has elapsed since the application of the light emitted from the first light source was started, the application of the light emitted from the second light source is started.

Advantageous Effects of Invention

According to the microbe inactivation processing method of the present invention, the inactivation processing can be performed on the target microbe present on or in the human body, while preventing or inhibiting damage to human body cells. Furthermore, the light emitted from the light source can be used with high efficiency, thus reducing the power requirements of the inactivation processing device. Since the optical filter transmits light having been incident at a large incident angle, the light having a large diffusion angle is allowed to exit through the optical filter, thus allowing the obtainment of a large effective irradiation area.

According to the cell activation processing method of the present invention, activation of the target cells can be reliably performed with high efficiency.

DESCRIPTION OF EMBODIMENTS

[Microbe Inactivation Processing Method]

Figure 1:
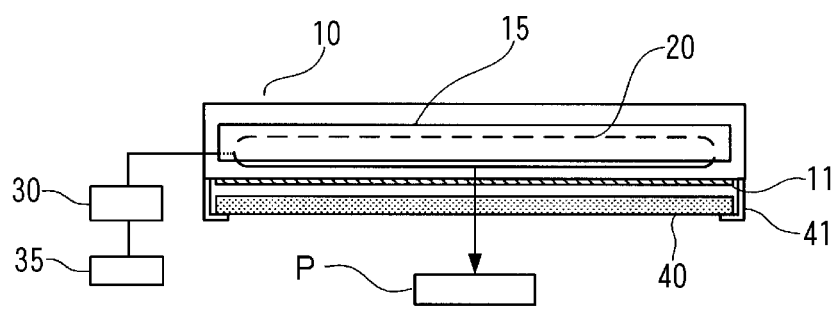
FIG. 1 is an explanatory view illustrating a configuration of an example of a microbe inactivation processing device used in the present invention.

FIG. 1 is an explanatory view illustrating a configuration of an example of a microbe inactivation processing device used in the present invention.

The microbe inactivation processing device (hereinafter also simply called "inactivation processing device") includes a casing 10 having a parallelepiped outer shape. One surface (bottom surface in FIG. 1) of the casing 10 is provided with a rectangular plate-shaped ultraviolet light transmission window 11 made of, for example, synthetic quarts glass, which transmits ultraviolet light.

In the casing 10, a rod-shaped excimer lamp 20, as a light source, is disposed to be opposite to the ultraviolet light transmission window 11. Behind the excimer lamp 20 in the casing 10, a trough-shaped reflective mirror 15 is disposed so as to enclose the excimer lamp 20, in order to reflect light from the excimer lamp 20 toward the ultraviolet light transmission window 11.

Since oxygen in air absorbs light having a wavelength of 200 nm or lower, for the purpose of preventing attenuation of the intensity of light from the excimer lamp 20, the inside of the casing 10 is purged with an inert gas such as a nitride ($N_2$) gas, as necessary.

A power supply unit 30 is connected to the excimer lamp 20 to supply the excimer lamp 20 with electric power. To the power supply unit 30, a control unit 35 is connected to control the power supply unit 30.

Outside the casing 10, a rectangular plate-shaped optical filter 40 is disposed in a position opposite to the ultraviolet light transmission window 11. The optical filter 40 is secured to the casing 10 with a securing member 41.

As the excimer lamp 20, an excimer lamp that emits light having a center wavelength of 190 to 230 nm can be used.

As concrete examples of the excimer lamp 20, may be mentioned a KrCl excimer lamp that emits light having a center wavelength of 222 nm, and a KrBr excimer lamp that emits light having a center wavelength of 207 nm.

Figure 2:
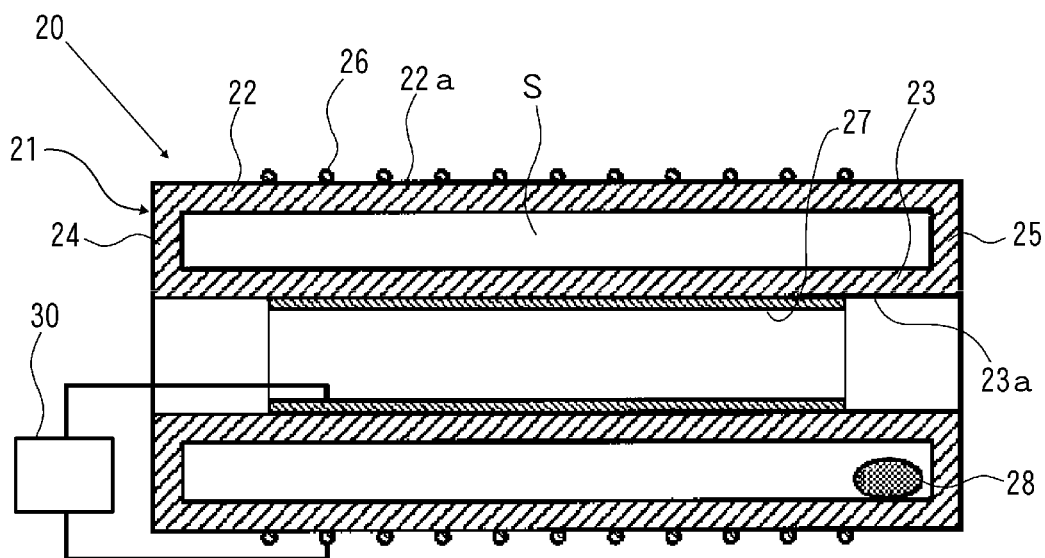
FIG. 2 is an explanatory cross-sectional view illustrating a configuration of an example of an excimer lamp.

FIG. 2 is an explanatory cross-sectional view illustrating a configuration of an example of the excimer lamp 20. The excimer lamp 20 includes an airtight discharge container 21 that has a first cylindrical dielectric wall member 22 (first wall member) and a second cylindrical dielectric wall member 23 (second wall member) disposed inside the first wall member 22 along a cylindrical axis of the first wall member 22. The outer diameter of the second wall member 23 is smaller than the inner diameter of the first wall member 22. In the discharge container 21, sealing walls 24 and 25 join both end portions of the first wall member 22 and the second wall member 23, and so a cylindrical discharge space S is formed between the first and second wall members 22 and 23. As a dielectric for the discharge container 21, for example, quartz glass can be used.

On the first wall member 22 of the discharge container 21, a net-shaped first electrode 26, such as, for example, a wire mesh, made of a conductive material is provided so as to be in close contact with an outer peripheral surface 22a of the first wall member 22. On the second wall member 23 of the discharge container 21, a film-shaped second electrode 27 made of aluminum is provided so as to cover an outer surface 23a of the second wall member 23. Each of the first and second electrodes 26 and 27 is connected to the power supply unit 30.

The discharge container 21 is filled with a discharge gas made of a mixture of krypton and chlorine or bromine. In the discharge container 21, a luminous element supplemental material 28 made of a metal chloride or metal bromide is disposed.

In the excimer lamp 20, by the application of a high frequency voltage between the first and second electrodes 26 and 27, dielectric barrier discharge occurs in the discharge space S in the discharge container 21. Therefore, in the discharge container 21, excimers are generated from krypton elements and chlorine elements or bromine elements, and excimer light emitted from the excimers is emitted to the outside from the mesh of the first electrode 26 through the first wall member 22.

When the excimer lamp 20 is a KrCl excimer lamp, excimer light emitted from the excimer lamp 20 has a center wavelength of, for example, 222 nm, and includes light having a wavelength within a wavelength range of 230 to 300 nm.

When the excimer lamp 20 is a KrBr excimer lamp, excimer light emitted from the excimer lamp 20 has a center wavelength of, for example, 207 nm, and includes light having a wavelength within a wavelength range of 230 to 300 nm.

When light emitted from the light source is incident at an incident angle of 0°, the optical filter 40 transmits at least a part of ultraviolet light having a wavelength within a range of not lower than 190 nm and not more than 230 nm, and transmits ultraviolet light having a wavelength within a range of more than 230 nm and not more than 237 nm, while blocking transmission of ultraviolet light having a wavelength out of a wavelength range of not lower than 190 nm and not more than 237 nm. "Blocking transmission of ultraviolet light" means that the intensity of the ultraviolet light after transmission of the optical filter comes to be 1/1000 or less, with respect to the intensity at a peak wavelength within a wavelength range of not lower than 190 nm and not more than 237 nm.

As such an optical filter 40, an optical filter having a dielectric multilayer film constituted of an $SiO_2$ film and an $Al_2O_3$ film, or an optical filter having a dielectric multilayer film constituted of an $HfO_2$ film and an $SiO_2$ film is preferably used.

Figure 3:
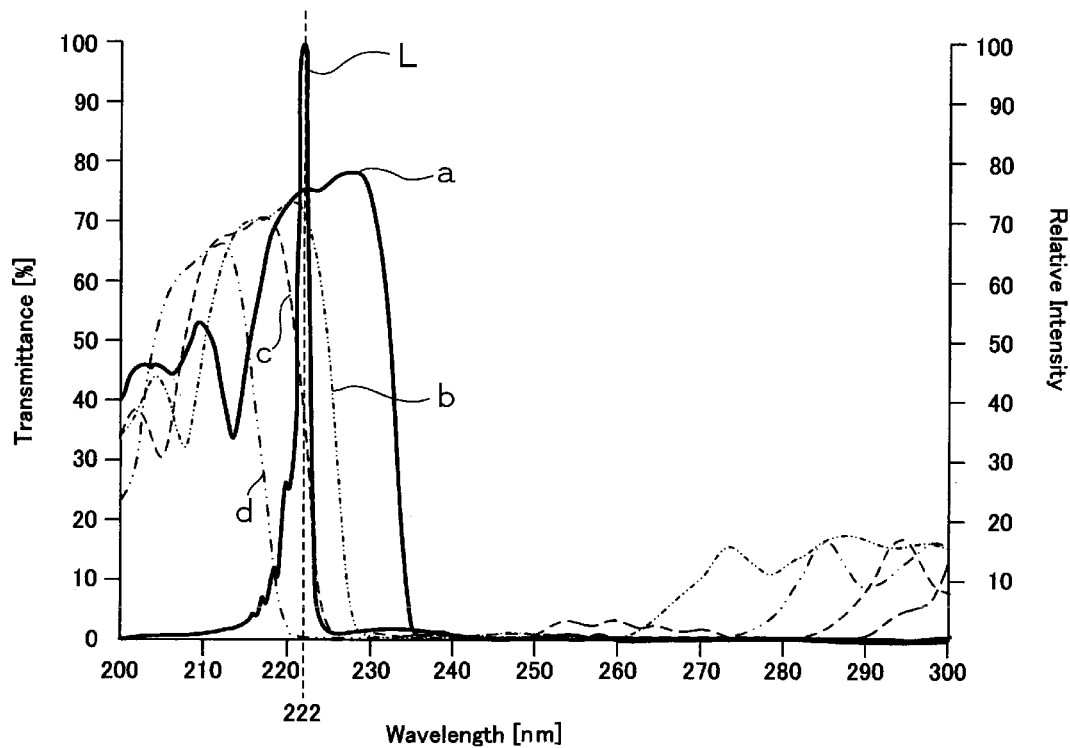
FIG. 3 is a graph showing spectral distribution of light transmittance of an example of an optical filter used in the present invention, together with the spectrum of a KrCl excimer lamp.

FIG. 3 is a graph showing spectral distribution of light transmittance of an example of the optical filter used in the present invention, together with the spectrum of a KrCl excimer lamp.

In FIG. 3, a curve "a" indicates a spectral distribution curve of light transmittance, when light is incident on the optical filter at an incident angle of 0°. A curve "b" indicates a spectral distribution curve of light transmittance, when light is incident on the optical filter at an incident angle of 25°. A curve "c" indicates a spectral distribution curve of light transmittance, when light is incident on the optical filter at an incident angle of 30°. A curve "d" indicates a spectral distribution curve of light transmittance, when light is incident on the optical filter at an incident angle of 40°. A curve "L" indicates the spectrum of the KrCl excimer lamp.

The optical filter 40 according to this example is composed of a synthetic quartz glass substrate and dielectric multilayer films, which are constituted of $SiO_2$ layers and $Al_2O_3$ layers laminated alternately, formed on both surfaces of the substrate. The number of the $SiO_2$ layers and the $Al_2O_3$ layers in the dielectric multilayer film is 230, and the total thickness thereof exceeds 10 μm.

In the optical filter 40, as shown in FIG. 3, when the incident angle is 0°, the transmittance of ultraviolet light having a wavelength of 222 nm (the peak wavelength of light emitted from the KrCl excimer lamp) is approximately 75%. However, when the incident angle is 25°, the transmittance is not less than 50%. When the incident angle is 30°, the transmittance is not less than 40%, and when the incident angle is 40°, the transmittance is several %.

In the optical filter 40, when the incident angle is 0°, the transmittance of ultraviolet light having a wavelength of 231 nm is approximately 68.5%, and the transmittance of ultraviolet light having a wavelength of 235 nm is approximately 4%.

Figure 4:
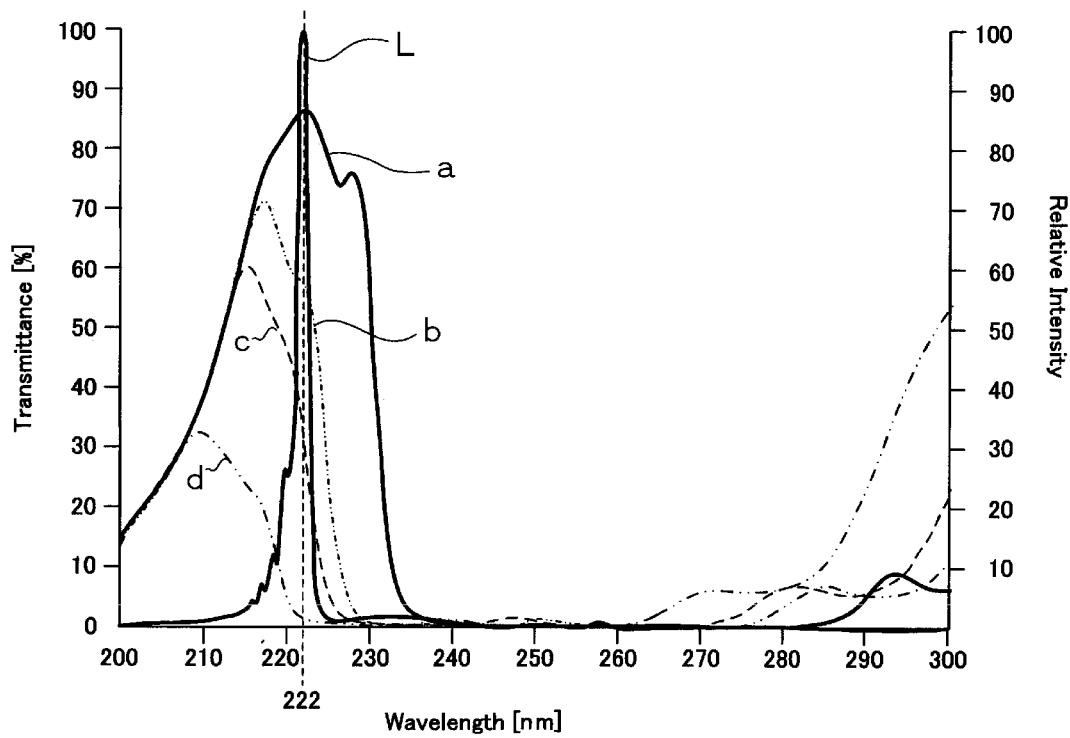
FIG. 4 is a graph showing spectral distribution of light transmittance of another example of the optical filter used in the present invention, together with the spectrum of the KrCl excimer lamp.

FIG. 4 is a graph showing spectral distribution of light transmittance of another example of the optical filter used in the present invention, together with the spectrum of the KrCl excimer lamp.

In FIG. 4, a curve "a" indicates a spectral distribution curve of light transmittance, when light is incident on the optical filter at an incident angle of 0°. A curve "b" indicates a spectral distribution curve of light transmittance, when light is incident on the optical filter at an incident angle of 25°. A curve "c" indicates a spectral distribution curve of light transmittance, when light is incident on the optical filter at an incident angle of 30°. A curve "d" indicates a spectral distribution curve of light transmittance, when light is incident on the optical filter at an incident angle of 40°. A curve "L" indicates the spectrum of the KrCl excimer lamp.

The optical filter 40 according to this example is composed of a synthetic quartz glass substrate and a dielectric multilayer film, which is constituted of $HfO_2$ layers and $SiO_2$ layers laminated alternately, formed on one surface of the substrate. In the dielectric multilayer film, the thickness of the $HfO_2$ layer is approximately 240 nm, the thickness of the $SiO_2$ layer is approximately 1460 nm, the number of the $HfO_2$ layers and the $SiO_2$ layers in total is 33, and the total thickness of the $HfO_2$ layers is 1700 nm. The other surface of the substrate is coated by AR coating using the $HfO_2$ layers and the $SiO_2$ layers.

In the optical filter 40, as shown in FIG. 4, when the incident angle is 0°, the transmittance of ultraviolet light having a wavelength of 222 nm (the peak wavelength of light emitted from the KrCl excimer lamp) is approximately 85%. However, when the incident angle is 25°, the transmittance is not less than 50%. When the incident angle is 30°, the transmittance is approximately 35%, and when the incident angle is 40°, the transmittance is several %.

In the optical filter 40, when the incident angle is 0°, the transmittance of ultraviolet light having a wavelength of 231 nm is approximately 35.6%, and the transmittance of ultraviolet light having a wavelength of 235 nm is approximately 2.5%.

Figure 5:
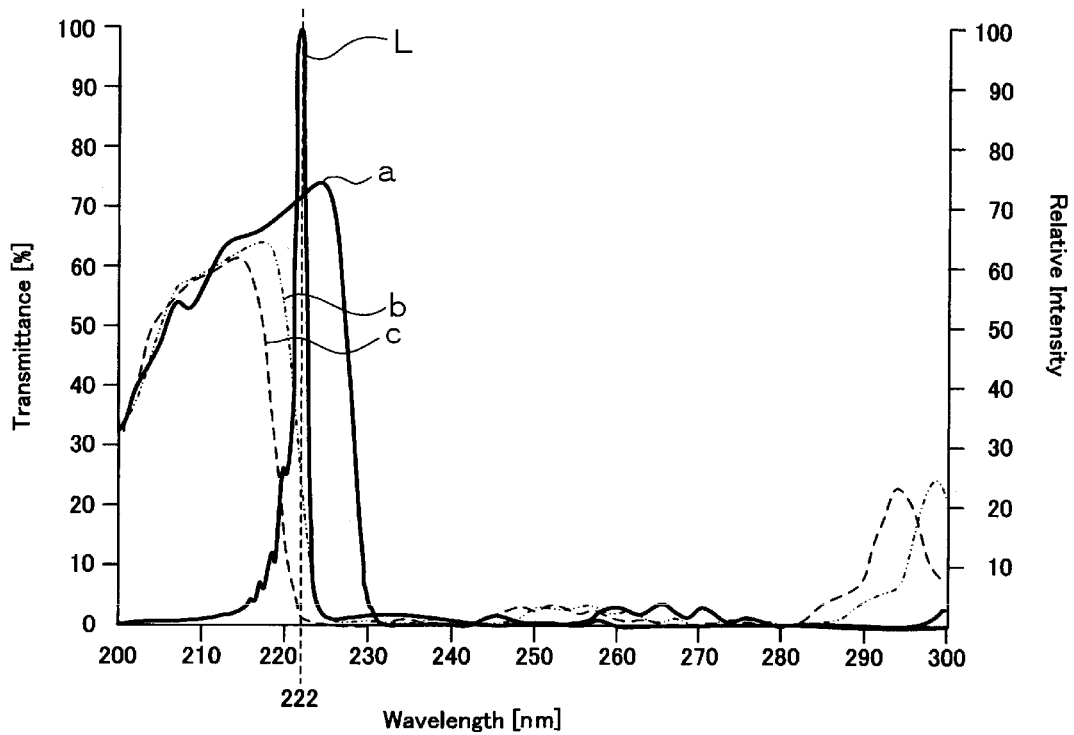
FIG. 5 is a graph showing spectral distribution of light transmittance of an optical filter for comparison with the another example, together with the spectrum of the KrCl excimer lamp.

FIG. 5 is a graph showing spectral distribution of light transmittance of an optical filter for comparison, together with the spectrum of the KrCl excimer lamp.

In FIG. 5, a curve "a" indicates a spectral distribution curve of light transmittance, when light is incident on the optical filter at an incident angle of 0°. A curve "b" indicates a spectral distribution curve of light transmittance, when light is incident on the optical filter at an incident angle of 25°. A curve "c" indicates a spectral distribution curve of light transmittance, when light is incident on the optical filter at an incident angle of 30°. A curve "L" indicates the spectrum of the KrCl excimer lamp.

The optical filter for comparison is composed of a synthetic quartz glass substrate and dielectric multilayer films, which are constituted of $SiO_2$ layers and $Al_2O_3$ layers laminated alternately, formed on both surfaces of the substrate. The number of the $SiO_2$ layers and the $Al_2O_3$ layers in the dielectric multilayer film is 230, and the total thickness thereof exceeds 10 μm.

In the optical filter for comparison, as shown in FIG. 5, when the incident angle is 0°, the transmittance of ultraviolet light having a wavelength of 222 nm (the peak wavelength of light emitted from the KrCl excimer lamp) is approximately 70%. However, when the incident angle is 25°, the transmittance is approximately 50%. When the incident angle is 30°, the transmittance is several %.

In the optical filter for comparison, when the incident angle is 0°, the transmittance of ultraviolet light having a wavelength of 231 nm is approximately 4%, and the transmittance of ultraviolet light having a wavelength of 235 nm is 0%.

By using the optical filter 40 having the optical characteristics as shown in FIG. 3 or 4, when the light emitted from the KrCl excimer lamp is applied to target microbes through the optical filter 40, the light can be effectively used, if the incident angle on the optical filter 40 is not more than 30°.

Since the optical filter 40 transmits light having been incident at a large incident angle, light having a large diffusion angle can be outputted through the optical filter 40, thus allowing the obtainment of a large effective irradiation area.

On the contrary, in the case of using the optical filter for comparison having optical characteristics as shown in FIG. 5, when the light emitted from the KrCl excimer lamp is applied to target microbes through the optical filter, light having an incident angle of more than 25° on the optical filter cannot be effectively used, thus making it difficult to obtain a large effective irradiation area.

The number of layers of the dielectric multilayer film having the $HfO_2$ layers and the $SiO_2$ layers is much smaller than that of dielectric multilayer film having the $SiO_2$ layers and the $Al_2O_3$ layers. Therefore, the optical filter that has the dielectric multilayer film having the $HfO_2$ layers and the $SiO_2$ layers can have a high transmittance with respect to the ultraviolet light having a wavelength of 222 nm (the peak wavelength of light emitted from the KrCl excimer lamp). Furthermore, since the number of layers of the dielectric multilayer film is small, the optical filter 40 that has a high cut wavelength reproducibility can be produced at a low cost.

From this viewpoint, the optical filter 40 that has the dielectric multilayer film having the $HfO_2$ layers and the $SiO_2$ layers is preferably used.

In the case of using the optical filter 40 that has the dielectric multilayer film having the $HfO_2$ layers and the $SiO_2$ layers, the total thickness of the $HfO_2$ layers is preferably not more than 500 nm. If the total thickness is less than 100 nm, light having a wavelength of not more than 200 nm cannot be sufficiently cut, and so the total thickness is preferably not less than 100 nm. By satisfying such conditions, the optical filter 40 having a high transmittance, for example, a transmittance of 80% or more, with respect to ultraviolet light having a wavelength in the vicinity of 222 nm (the peak wavelength of light emitted from the KrCl excimer lamp) can be obtained.

The KrCl excimer lamp is used as the light source in the foregoing example. However, even when a KrBr excimer lamp is used as the light source, the optical filter 40 that blocks transmission of light having a wavelength out of the wavelength range of 190 to 237 nm and has a maximum transmittance in the vicinity of 207 nm, which is the peak wavelength of the KrCl excimer lamp, can be designed, thus allowing the obtainment of the same effects as in the case of using the KrCl excimer lamp.

On the other hand, in the present invention, the optical filter 40 transmits ultraviolet light having a wavelength of more than 230 nm and not more than 237 nm. It has been confirmed that the application of such ultraviolet light does not damage human body cells, as described below.

Figure 6:
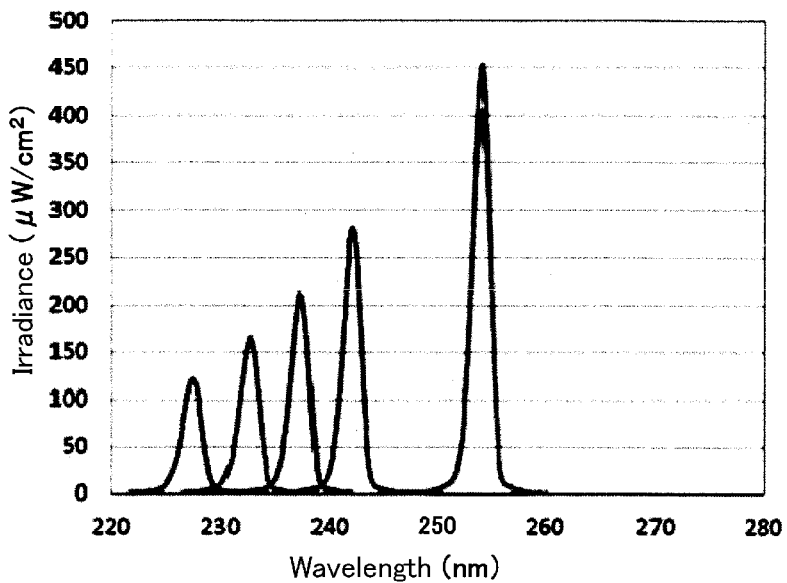
FIG. 6 is a graph of the spectrum of ultraviolet light applied to mice, in a test to verify that ultraviolet light having a wavelength of more than 230 nm and not more than 237 nm does not damage cells of the mice.

Light emitted from a Xe lamp was divided by a spectral device into five types of rays of ultraviolet light (a full width at half maximum of 2 nm) each of which had a peak wavelength of 227 nm, 232 nm, 237 nm, 242 nm, or 254 nm. FIG. 6 shows the spectrum of each ultraviolet ray. The ultraviolet ray of each wavelength was applied to mice's backs in which their hairs had been shaved in advance.

In the above-described circumstances, a dose of the ultraviolet ray of each wavelength was set at 150 $mJ/cm^2$ and 300 $mJ/cm^2$. As is apparent from FIG. 6, since irradiance varies from one ultraviolet ray to another, an irradiation time of each ultraviolet ray was adjusted so as to have the set dose.

After each ultraviolet ray was applied to the mice, the presence or absence of generation of cyclobutane pyrimidine (CPD) at irradiation areas of the mice was checked. Since CPD is generated due to DNA damage induced by ultraviolet light, CPD serves as an indication for damage to cells.

As a result, when the ultraviolet ray having a wavelength of 227 nm, 232 nm, or 237 nm was applied, CPD was not generated in either of the doses of 150 mJ/cm$^2$ and 300 mJ/cm$^2$.

On the other hand, when the ultraviolet ray having a wavelength of 242 nm or 254 nm was applied, CPD was generated in either of the doses of 150 mJ/cm$^2$ and 300 mJ/cm$^2$.

As a result of above, it is understood that even if ultraviolet light having a wavelength of more than 230 nm and not more than 237 nm is applied, the application does not damage human body cells.

In the inactivation processing method of the present invention, the excimer lamp 20 are turned on by supplying electric power from the power supply unit 30 to the excimer lamp 20. Light emitted from the excimer lamp 20 radiates outside of the casing 10 through the ultraviolet light transmission window 11, and thereafter is applied to a target portion P through the optical filter 40. Therefore, target microbes, such as bacteria, that are present in the target portion P on or in the human body are subjected to inactivation processing.

To use the inactivation processing method according to the present invention as a device for inactivating target microbes present on a human body, the control unit 35 preferably controls a dose of light per irradiation within a wavelength range of 190 to 237 nm to be applied to the target microbes at 10 mJ/cm$^2$ to 1000 mJ/cm$^2$, and particularly preferably at 10 mJ/cm$^2$ to 50 mJ/cm$^2$. As a method to control the dose, a method by which the value of electric power supplied to the excimer lamp 20 is adjusted, or a method by which a time to supply electric power to the excimer lamp 20, i.e., a light irradiation time to the target microbes is adjusted can be used.

When the dose is lower than 10 mJ/cm$^2$, it may be difficult to inactivate the target microbes present on the human body.

The optical filter 40 having the dielectric multilayer film is difficult to completely block light having a wavelength out of a wavelength range of 190 to 237 nm, owing to its characteristic. Therefore, when a dose per day exceeds 1000 mJ/cm$^2$, the dose of the light having a wavelength out of the wavelength range of 190 to 237 nm increases, and may cause damage to human body cells.

To use the inactivation processing method according to the present invention as a device for inactivating target microbes present in a human body (particularly, in an injury or an operative field), the control unit 35 preferably controls a dose of light per irradiation to be applied to the target microbes at 300 mJ/cm$^2$ to 1000 mJ/cm$^2$.

When the dose is lower than 300 mJ/cm$^2$, it may be difficult to inactivate the target microbes present in the human body.

As described above, according to the inactivation processing method of the present invention, since the ultraviolet light from the excimer lamp 20, i.e., the light source, is applied to the target microbes through the optical filter 40 having specific optical characteristics, the target microbes present on or in the human body can be subjected to the inactivation processing, while damage to human body cells is prevented or inhibited. Furthermore, the light emitted from the excimer lamp 20, i.e., the light source, can be used with high efficiency, thus reducing the power requirements of the inactivation processing device. Since the optical filter 40 transmits light having been incident at a large incident angle, light having a large diffusion angle can be outputted through the optical filter 40, thus allowing the obtainment of a large effective irradiation area.

[Cell Activation Processing Method]

The present invention is not limited to the inactivation processing method, but may be applied to, for example, the following field.

In recent years, as a method for reducing bedsore areas and diabetic ulcer areas (hereinafter collectively called "disease areas"), a method for applying infrared light to the disease areas has received attention. In this method, the application of the infrared light activates cells in the disease area, and the disease area is thereby reduced.

If germs (bacteria) are present in the disease area, the reduction in the bedsore area or the diabetic ulcer area, using the activation of the cells, does not proceed. This is because the application of the infrared light activates the germs (bacteria) too, and so the activated germs (bacteria) inhibit the activation of the cells in the bedsore area or the diabetic ulcer area.

Accordingly, the disease area is desired to be subjected to inactivation processing of the germs (bacteria), while being subjected to activation processing of the cells in the disease area by applying the infrared light. Considering a load on the disease area, a method using the application of ultraviolet light, which is a noncontact method, is preferable as the inactivation processing. Although ultraviolet light of UV-C (200 to 280 nm) is effective at inactivating the germs (bacteria), it is known that UV-C (particularly, 254 nm) damages DNA of humans and animals, and so the method using the application of ultraviolet light is not adopted as the inactivation processing of the germs (bacteria) present in the disease area.

Adopting the above-described structure of the inactivation processing device in a cell activation processing device makes it possible to subject the germs (bacteria) present in the bedsore area, the diabetic ulcer area and the like to inactivation processing without damaging the DNA of the humans and the animals. Therefore, the cell activation processing can be efficiently performed on the disease area.

Figure 7A:
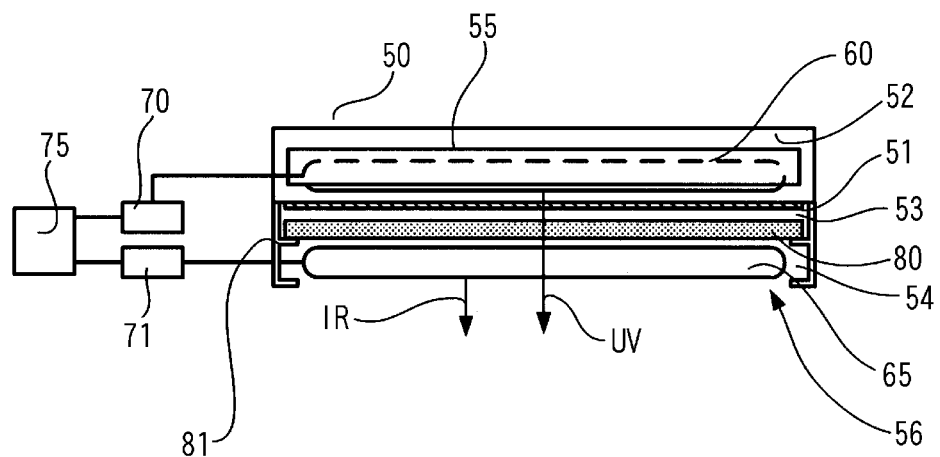
FIGS. 7A and 7B are explanatory views illustrating a configuration of an example of a cell activation processing device used in the present invention.
Figure 7B:
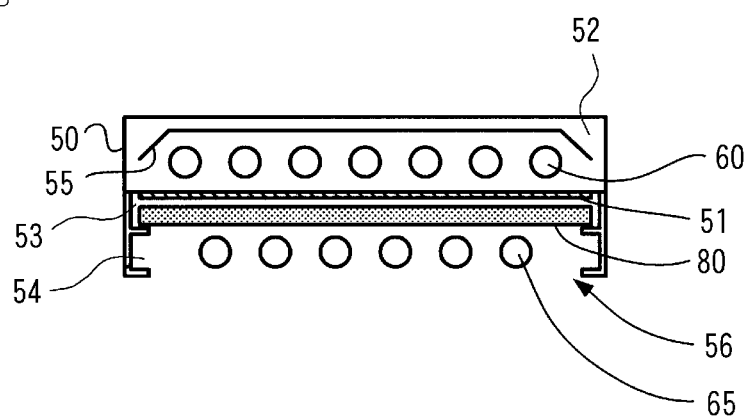

FIGS. 7A and 7B are explanatory views illustrating a configuration of an example of a cell activation processing device used in the present invention.

FIG. 7A is an explanatory cross-sectional view of a casing of the cell activation processing device that is cut along a longitudinal direction of an excimer lamp, and FIG. 7B is an explanatory cross-sectional view of the casing of the cell activation processing device that is cut in a direction orthogonal to the longitudinal direction of the excimer lamp.

The cell activation processing device includes a casing 50 having a parallelepiped outer shape. In the casing 50, a first space portion 52 that mainly contains a first light source configured to emit ultraviolet light, a second space portion 53 that contains an optical filter 80, and a third space portion 54 that mainly contains a second light source configured to emit infrared light are formed so as to be arranged in this order.

A rectangular plate-shaped ultraviolet light transmission window 51 made of, for example, synthetic quarts glass, which transmits ultraviolet light, is provided between the first space portion 52 and the second space portion 53.

In the first space portion 52, at least one rod-shaped excimer lamp 60 as a first light source is disposed to be opposite to the ultraviolet light transmission window 51. In the example illustrated in the drawing, a plurality of excimer lamps 60 are arranged in parallel at a distance from each other. The excimer lamps 60 and the optical filter 80, which will be described later, constitute a first light source unit.

Behind the excimer lamps 60 in the first space portion 52, a trough-shaped reflective mirror 55 is disposed so as to enclose the excimer lamps 60, in order to reflect light from the excimer lamps 60 toward the ultraviolet light transmission window 51.

Since oxygen in air absorbs light having a wavelength of not more than 200 nm, for the purpose of preventing attenuation of the intensity of light from the excimer lamps 60, the inside of the first space portion 52 is purged with an inert gas, such as a nitride ($N_2$) gas, as necessary.

A first power supply unit 70 is connected to the excimer lamps 60, to supply the excimer lamps 60 with electric power. To the first power supply unit 70, a control unit 75 is connected to control the first power supply unit 70.

In the second space portion 53 adjoining the first space portion 52, the rectangular plate-shaped optical filter 80 is disposed in a position opposite to the ultraviolet light transmission window 51. The optical filter 80 is secured to the casing 50 with a securing member 81.

At least one rod-shaped second light source 65 configured to emit infrared light is disposed to be opposite to the optical filter 80 in the third space portion 54, which adjoins the second space portion 53 on the opposite side to the first space portion 52. In the example illustrated in the drawing, a plurality of second light sources 65 are arranged in parallel at a distance from each other. The second light sources 65 constitute a second light source unit. Each of the second light sources 65 is disposed between the excimer lamps 60 next to each other, when viewed in a plan view of the cell activation processing device.

In the third space portion 54, a light outputting unit 56 that outputs the ultraviolet light emitted from the excimer lamps 60 through the optical filter 80 and the infrared light emitted from the second light sources 65 is provided in a position opposite the second light sources 65.

A second power supply unit 71 configured to supply the second light sources 65 with electric power is connected to the second light source 65s. To the second power supply unit 71, the control unit 75 that controls the second power supply unit 71 is connected. In the example illustrated in the drawing, the common control unit 75 is configured to control both of the first power supply unit 70 and the second power supply unit 71, but the first power supply unit 70 and the second power supply unit 71 may be configured to be controlled by individual control units.

The excimer lamps 60, which constitute the first light source, and the optical filter 80 are identical to the excimer lamp 20 and the optical filter 40 in the above-described inactivation processing device, respectively.

As the second light source 65, any type of light source, for example, a halogen lamp, an LED configured to emit infrared light or the like can be used as long as the light source is capable of emitting required infrared light.

In the cell activation processing method of the present invention, the excimer lamps 60 are turned on by supplying electric power from the first power supply unit 70 to the excimer lamps 60 contained in the first space portion 52. Ultraviolet light (indicated by an arrow UV in FIG. 7A) emitted from the excimer lamps 60 is applied to a target area, such as a disease area, through the ultraviolet light transmission window 51, the optical filter 80 contained in the second space portion 53, the third space portion 54, and the light outputting unit 56. Therefore, microbes, including bacteria and the like, that are present in the target area are subjected to inactivation processing. The application of the ultraviolet light excites and activates cells in the target area.

On the other hand, the second light sources 65 contained in the third space portion 54 are turned on by supplying electric power from the second power supply unit 71 to the second light sources 65. Infrared light (indicated by an arrow IR in FIG. 7A) emitted from the second light sources 65 is applied to the target area through the light outputting unit 56. Cell activation processing is thereby performed on the target area.

In the case of performing the cell activation processing on the light irradiation area of the human body, the control unit 75 preferably controls a dose of light per irradiation within a wavelength range of 190 to 237 nm to be applied to microbes on a surface of the human body at 10 $mJ/cm^2$ to 1000 $mJ/cm^2$, and particularly preferably at 10 $mJ/cm^2$ to 50 $mJ/cm^2$.

In the case of performing the cell activation processing by applying light to the inside of the human body, the control unit 75 preferably controls a dose of light per irradiation within a wavelength range of 190 to 237 nm to be applied to the target microbes at 300 $mJ/cm^2$ to 1000 $mJ/cm^2$.

The control unit 75 may control the first power supply unit 70 and the second power supply unit 71 to concurrently turn on the excimer lamps 60 and the second light sources 65. However, the first power supply unit 70 is preferably controlled to turn on the excimer lamps 60, and after a predetermined time has elapsed since the excimer lamps 60 were turned on, the second power supply unit 71 is preferably controlled to turn on the second light sources 65.

In the case of concurrently turning on the excimer lamps 60 and the second light sources 65, for example, when the temperature of the target area becomes approximately 37° C., microbes including bacteria and the like are disadvantageously activated, and thus the inactivation of the microbes and the activation of cells may not sufficiently proceed. Therefore, the excimer lamps 60 are preferably turned on prior to turning-on of the second light sources 65 to perform the inactivation processing on the microbes, including bacteria and the like, present in the target area.

A time from the start of turning on the excimer lamps 60 to the start of turning on the second light sources 65 corresponds to, for example, a time until a dose of the ultraviolet light comes to 50 to 150 $mJ/cm^2$.

In the case of turning on the second light sources 65, after a predetermined time has elapsed since the excimer lamps 60 were turned on, the excimer lamps 60 may be turned off or continuously turned on, while the second light sources 65 are turned on.

When the excimer lamps 60 are continuously turned on, while the second light sources 65 are turned on, the cell activation processing can be efficiently performed by a synergetic effect between ultraviolet light irradiation and infrared light irradiation.

According to the cell activation processing method of the present invention, since the cell activation processing is performed on the target area, while or after the inactivation processing of the microbes present in the target area is performed, it is possible to reliably perform the activation of the target cells with high efficiency.

Since the ultraviolet light from the excimer lamps 60 is applied to the target area through the optical filter 80 having the specific optical characteristics, the inactivation processing of the microbes can be performed while preventing or inhibiting damage to the target cells. The light emitted from the excimer lamps 60 can be used with high efficiency, and therefore it is possible to reduce the power requirements of the cell activation processing device. Furthermore, since the optical filter 80 transmits light having been incident at a large incident angle, light having a large diffusion angle can be outputted through the optical filter 80, thus allowing the obtainment of a large effective irradiation area.

The present invention is not limited to the above embodiments, but may be variously modified.

For example, when the light emitted from the light source (or the first light source) is incident at an incident angle of 0°, the optical filter may transmit at least a part of ultraviolet light having a wavelength within a range of not lower than 190 nm and not more than 230 nm, and transmit at least apart of ultraviolet light having a wavelength within a range of more than 230 nm and not more than 237 nm, and the optical filter blocks transmission of ultraviolet light having a wavelength within wavelength ranges of UV-B and UV-C excluding a wavelength range of not lower than 190 nm and not more than 237 nm.

REFERENCE SIGNS LIST

10 casing
11 ultraviolet light transmission window
15 reflective mirror
20 excimer lamp
21 discharge container
22 first wall member
22a outer peripheral surface
23 second wall member
23a outer surface
24, 25 sealing wall
26 first electrode
27 second electrode
28 luminous element supplemental material
30 power supply unit
35 control unit
40 optical filter
41 securing member
50 casing
51 ultraviolet light transmission window
52 first space portion
53 second space portion
54 third space portion
55 reflective mirror
60 excimer lamp
65 second light source
70 first power supply unit
71 second power supply unit
75 control unit
80 optical filter
81 securing member
P sterilization target portion
S discharge space

The invention claimed is:

1. A microbe inactivation processing method comprising:
a step of applying light emitted from a light source through an optical filter onto a human body, with the light source configured to emit light having a wavelength within a wavelength range of 190 nm to 237 nm, in order to perform inactivation processing of a target microbe on the human body, wherein
when the light emitted from the light source is incident on the optical filter at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength outside of a wavelength range of not lower than 190 nm and not more than 237 nm.

2. The microbe inactivation processing method of claim 1, wherein when the light emitted from the light source is incident on the optical filter at an incident angle of 0°, the optical filter transmits at least a part of ultraviolet light having a wavelength within the range not lower than 190 nm and not more than 230 nm, and transmits at least a part of the ultraviolet light having a wavelength within the range of not lower than 232 nm and not more than 237 nm.

3. The microbe inactivation processing method of claim 2, wherein cyclobutane pyrimidine is not produced with application of light in the range of not lower than 232 nm and not more than 237 nm.

4. The microbe inactivation processing method of claim 1, wherein the energy of the applied light is in a range 10 mJ/cm2 to 1000 mJ/cm2.

5. A microbe inactivation processing method comprising:
a step of applying light emitted from a light source through an optical filter onto a human body, with the light source configured to emit the light having a wavelength within a wavelength range of 190 nm to 237 nm, in order to perform inactivation processing of a target microbe on the human body with an energy of 10 mJ/cm2 to 1000 mJ/cm2, wherein
when the light emitted from the light source is incident on the optical filter at an incident angle of 0°, the optical filter transmits at least a part of ultraviolet light having a wavelength within a range of not lower than 190 nm and not more than 230 nm, and transmits at least a part of ultraviolet light having a wavelength within a range of more than 230 nm and not more than 237 nm, and the optical filter blocks transmission of ultraviolet light having a wavelength within wavelength ranges of UV-B and UV-C excluding a wavelength range of not lower than 190 nm and not more than 237 nm.

6. The microbe inactivation processing method of claim 5, wherein when the light emitted from the light source is incident on the optical filter at an incident angle of 0°, the optical filter transmits at least a part of ultraviolet light having a wavelength within the range not lower than 190 nm and not more than 230 nm, and transmits at least a part of the ultraviolet light having a wavelength within a range of not lower than 232 nm and not more than 237 nm.

7. The microbe inactivation processing method of claim 6, wherein cyclobutane pyrimidine is not produced with application of light in the range of not lower than 232 nm and not more than 237 nm.

* * * * *